United States Patent
Bonne et al.

[11] Patent Number: 5,869,749
[45] Date of Patent: Feb. 9, 1999

[54] MICROMACHINED INTEGRATED OPTO-FLOW GAS/LIQUID SENSOR

[75] Inventors: Ulrich Bonne, Hopkins; Barrett E. Cole, Bloomington; Robert E. Higashi, Shorewood, all of Minn.

[73] Assignee: Honeywell Inc., Minneapolis, Minn.

[21] Appl. No.: 841,748

[22] Filed: Apr. 30, 1997

[51] Int. Cl.⁶ .......................... G01N 21/35; G01N 21/37; G01N 21/17; G01N 21/03
[52] U.S. Cl. ...................... 73/53.01; 73/23.31; 73/24.02; 73/31.01; 73/31.02; 73/31.03; 73/31.04; 73/31.05; 73/61.79; 73/64.53; 250/339.12; 250/339.13; 250/341.1
[58] Field of Search .............................. 73/23.31, 24.02, 73/25.01, 25.05, 31.01, 31.02, 31.03, 31.04, 31.05, 53.01, 61.41, 61.43, 61.45, 61.76, 61.79, 64.53; 250/339.01, 339.06, 339.12, 339.13, 341.1

[56] References Cited

U.S. PATENT DOCUMENTS

| | | | |
|---|---|---|---|
| 3,659,452 | 5/1972 | Atwood et al. | 73/31.04 |
| 4,958,076 | 9/1990 | Bonne et al. | 250/339.13 X |
| 5,444,249 | 8/1995 | Wong | 250/339.13 X |
| 5,600,148 | 2/1997 | Cole et al. | |
| 5,747,808 | 5/1998 | Wong | 250/339.13 X |

FOREIGN PATENT DOCUMENTS

| | | | |
|---|---|---|---|
| 4116280 | 12/1991 | Germany. | |
| 4208135 | 9/1993 | Germany. | |
| 4224518 | 3/1996 | Germany. | |
| 9-089773 | 4/1997 | Japan. | |
| 1352977 | 5/1974 | United Kingdom. | |
| 22045 | 8/1995 | WIPO | 250/339.13 |
| 24831 | 8/1996 | WIPO | 73/24.02 |

*Primary Examiner*—Daniel S. Larkin
*Attorney, Agent, or Firm*—John G. Shudy, Jr.

[57] ABSTRACT

A micromachined integrated opto-fluidic or opto-acoustic sensor having a rapidly intensity-varying or pulsing light source, an interference filter, a gas cavity, which may or may not be an optical and/or acoustic resonator tuned to a particular wavelength of light, or sound frequency, into which the detected gas can diffuse into via a filter, and a fluidic or pressure sensor to detect the heating and cooling, and the resulting expansion and contraction of the gas due to the absorption of light at the particular wavelength by the specific gas being detected. The presence of other gases is inferred from the detected gas.

27 Claims, 5 Drawing Sheets

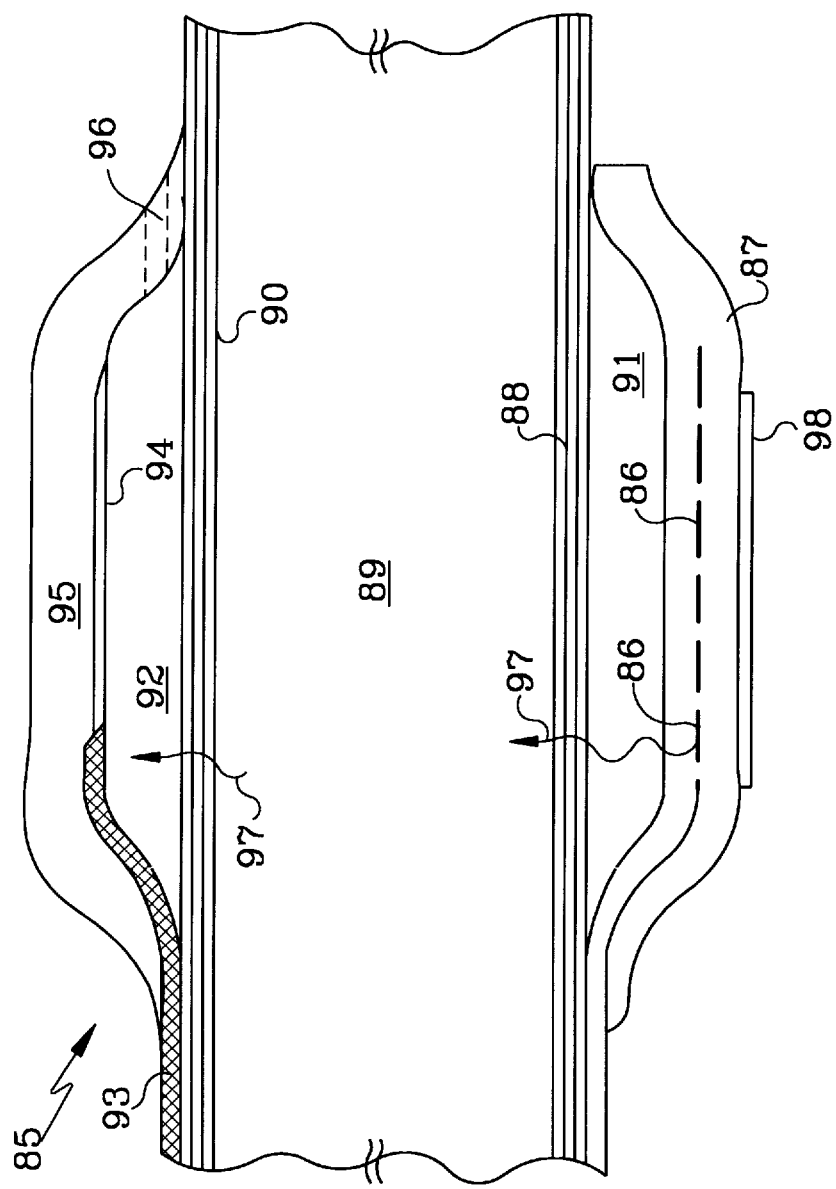

MICROMACHINED INTEGRATED OPTO-FLOW GAS/LIQUID SENSOR

BACKGROUND

The invention pertains to gas sensors and particularly to toxic gas sensors. More particularly, the invention pertains to micromachined integrated circuit gas and liquid sensors.

Related art devices for sensing toxic gases such as CO, NO, $NO_2$, and VOCs generated by combustion processes have been based on sensors indicating changes in metal oxide film conductivity, chemiluminescence, fluorescence, various forms of IR absorption, and so forth. These sensors have been either too costly, unstable, or insensitive to meet the requirements of a low-cost, reliable toxic gas sensor. Their sensing such toxic gases in concentrations that are commensurate with the levels at which they can be harmful to health and life is difficult, especially if it is to be done via low-cost, affordable, and reliable sensors. Often the older gas engines or heaters, operated by budget-minded users, are most likely to be a source of toxic gases which endanger these users and others. These users are the ones most unlikely to buy toxic gas indicators, unless someone manages to bring affordable and appropriate technology to them.

SUMMARY OF THE INVENTION

The present invention provides a new, useful, low-cost, reliable, and "conservative" indication of the presence of a toxic gas or objectionable constituents of combustion products. It is not necessary to directly measure the toxic or objectionable gases, if one can identify a phenomenon that would indicate or infer their presence with a meaningful probability level.

Carbon dioxide ($CO_2$) indicates the presence of objectionable concentrations of combustion products. $CO_2$ is generated by known combustion processes, in concentrations that are 10 to 100 times higher than those of CO, $NO_x$, or volatile organic compounds (VOCs). Yet one can measure $CO_2$ at concentration levels that are 3 to 30 times lower than the above-noted gases, especially via non-dispersive infrared (NDIR) sensing.

The present sensor provides more reliable, affordable and sensitive detection than direct NDIR sensing of toxic gases. It also provides additional detection/alarm protection against high $CO_2$ concentrations.

The sensor takes advantage of the indirect indication of toxic combustion products, such as CO, $NO_x$, and VOCs via $CO_2$ detection, and a low-cost, integrated optical sensor design made available at a reasonable price to meet the toxic gas sensing needs of users of unvented space heaters (or kitchen stoves) and the needs of automobile drivers that wish to detect exhaust fumes from cars or near them.

Combustion products, especially those from gasoline or diesel fuel are known to consist of 5–15% $Co_2$, 10–20% $H_2O$, 0–10% $O_2$, 70–80% $N_2$, 0.001 to 0.4% $NO_x$, 0.001 to 0.2% CO (CO in worn or maladjusted automotive engines may be up to 2%), and 0.001 to 0.3% hydrocarbons (HC), i.e., $CO_2$ concentrations always predominate. Still, dilution of exhaust gas of the car in front is expected to be 10 to 1000-fold before reaching the cabin air intake of the following car, so that the $CO_2$ concentration is likely to be 0.005 to 1.5%, which is measurable, while the toxic gas concentration is only in the 0.0001 to 0.04% range. The latter concentrations are much more difficult to measure, and especially so with low-cost sensors, which would often not begin to sense those gases in spite of being present in concentrations that cause discomfort or adverse health effects.

The integrated design of the present sensor enhances its ruggedness, portability, manufacturability, and affordability. The sensor cell, detector, and optical filter are integrated into one micromachined unit which is of lower cost, i.e., more affordable and more widely applicable than related-art sensors. The present sensor is more compact and therefore more rugged, more portable, and of faster response. The faster response is due to the smaller cavity and ability to operate at higher source frequencies. The flow detector features a much smaller flow channel, 10–25 micrometers (microns) versus 150 to 500 microns for related art devices. The total integrated sensor system is 10 to 100 times smaller than the related art sensors, which makes the present system more affordable, portable, faster response, and versatile. The present detectors are also 10 to 100 times less costly than the related-art detectors.

In summary, the invention is a low-cost opto-fluidic or opto-acoustic sensing system, which is a micromachined integrated sensor, which has a rapidly pulsing, thin-film light or heat source, an appropriate multi-layer interference filter (IF), anti-reflective (AR) coatings, and a specially etched silicon wafer, via a sacrificial layer, to form a sample gas cavity, which may be an optically or acoustically tuned resonator to the absorption wavelength of the gas to be detected, into which the sample gas can diffuse in and out via a suitable fluid filter such as a stainless steel frit which has a porosity that is optimized by a certain compression of the frit, and a flow sensor (thermal microanemometer) or microphone (piezoresistive sensing film) embedded in a wall of the cavity.

BRIEF DESCRIPTION OF THE DRAWING

FIG. 5 shows another integrated gas sensor.

DESCRIPTION OF THE EMBODIMENTS

Figure 1:
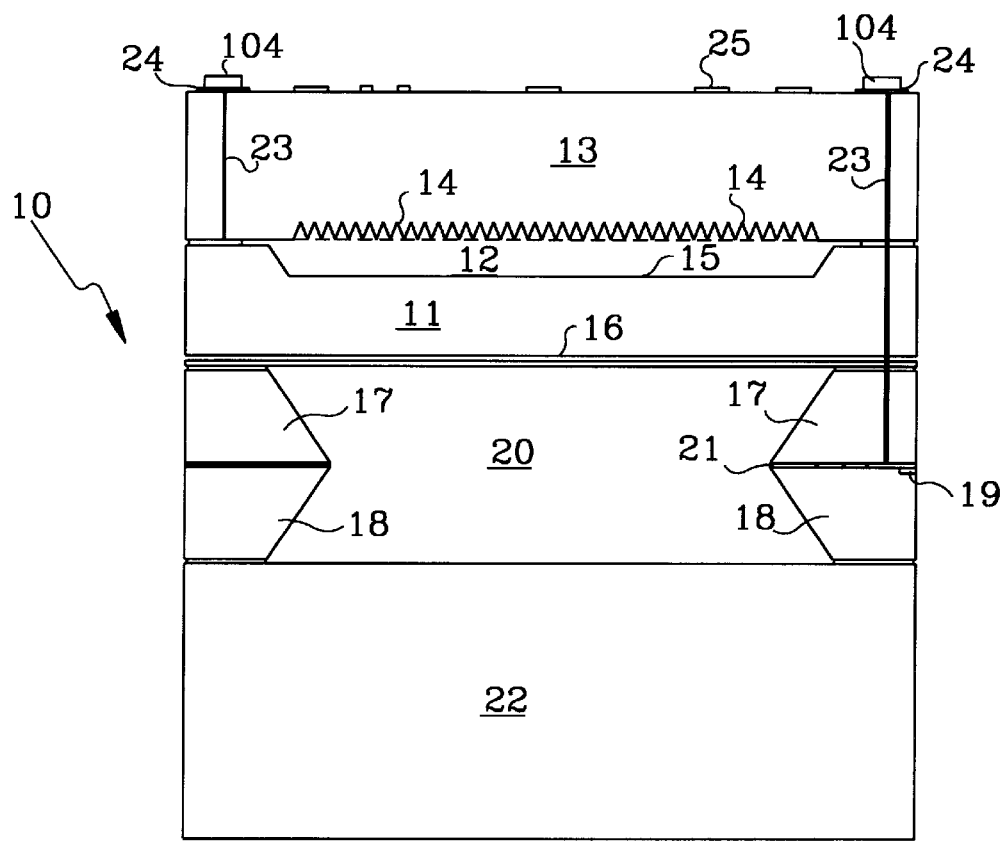
FIG. 1 reveals an integrated opto-fluidic gas sensor.

FIG. 1 is a diagram that shows a basic structure of inferential gas sensor 10. Silicon wafer 11 has an etched space 12 on one side. On that side having depression 12 is attached a silicon wafer 13 having a set of microemitters 14 on the side facing wafer 11. Wafer 11 may be instead a glass plate which could provide for better optical performance in terms of filtering some infrared (IR) wavelengths. Formed on the surface or side of wafer 11 adjacent to microemitters 14 is an antireflective (AR) coating 15. On the other side of wafer 11 is a narrow band pass interference filter (IF) 16 designed to pass only infrared light having a wavelength that is the same as the absorption wavelength (4.3 microns) of $CO_2$ or of the chosen gas to be detected (3.4 microns for VOC, 4.6 microns for CO, and so forth). The AR and IF coatings or films may be interchanged in location with each other. Silicon wafer 17 is bonded or attached to filter 16 and a flow sensor 19 is formed on silicon wafer 17. Silicon wafer 18 is bonded to wafer 17. Silicon wafers 17 and 18 are etched to form a cavity 20. Flow sensor 19 is situated in a pathway 21 between cavity 20 and the ambient volume or space external to sensor 10. Gas or air can flow in and out of cavity 20 via pathway or channel 21. A porous gas filter 22, which permits diffusion of gas from the ambient space into cavity 20, is bonded to wafer 18 thereby completing the forming of cavity 20. Filter 22 may be a wafer having a large number of small etched holes or a polymer, ceramic, or stainless steel frit, as examples. Preferred is a stainless steel frit compressed to optimal porosity. Microemitters 14 and flow sensor 19 are connected through the wafer conductors, contacts, or vias 23 to contact pads 24, are only for contacts to external power and signal output. Gaskets 104 may be formed on contacts 24, for the purposes of electrical communication with another wafer formed over wafer 13, upon which electronics may be situated. Such gaskets may have the properties of electrical conduction in essentially one axis such as up and down and not sideways. Formed on wafer 13 may be an integrated circuit (IC) or an application specific integrated circuit (ASIC) 25 for providing electronics for processing signals from flow sensor 19.

Microemitter 14 is a 32×32 array of microemitters that function as a light source or heater for sensor 10. The array 14 surface is about 12 times, its total emission is about 0.5 times but its 4.3 micron emission is 2.8 times that of a mini-tungsten light bulb. Cavity 20 is about 1×1×1 or 2×2×1 millimeters (mm). Cavity 20 cannot be too small because thermal quenching would occur, thus reducing the sensitivity of gas sensor 10. Flow sensor channel 21 is about 10–25 microns wide.

Figure 2:
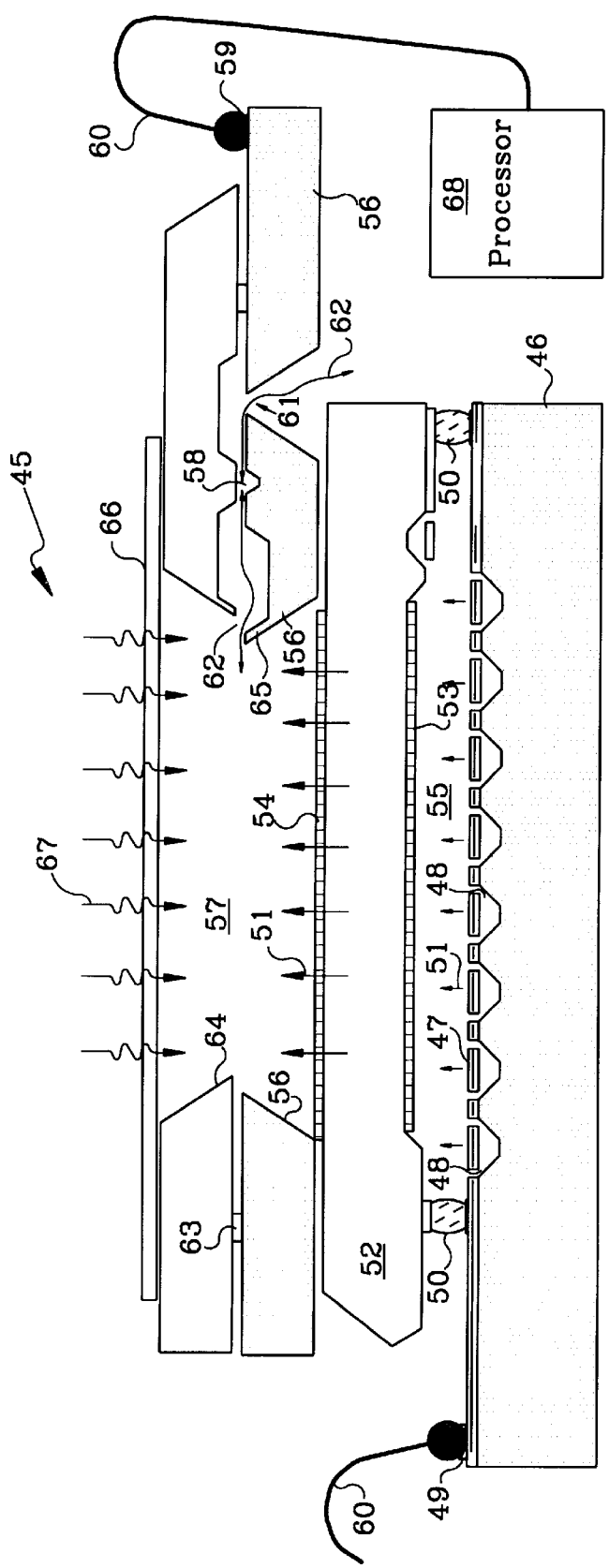
FIG. 2 shows another version of the opto-fluidic gas sensor.

FIG. 2 is a cross-section diagram of opto-fluidic gas sensor 45. Silicon wafer 46 is about 5×5 mm square and about 500 microns thick. Wafer 46, like wafer 13 of FIG. 1, has formed on it a heater or light source 47 of IR radiation. Source 47 is fabricated from a high refractory material such as a metal oxide or ceramic-like material. Grooves or pits 48 are etched in wafer 46 to provide heat dissipation for source 47. Leads 60, about 25 microns thick, are attached to contacts 49 for providing an AC signal at a frequency from 10 to 100 hertz to activate source 47 so as to emanate radiation or illumination 51. Spacers 50 are formed on the periphery of chip or wafer 46. A silicon wafer 52 about 500 microns thick is formed. Wafer 52 may instead be a glass plate. An AR film coating 53 is formed on a first side of wafer 52 and a narrow band pass IF multiple stack layer 54 for passing 4.3 microns of light is formed on a second side of wafer 52. AR film layer 53 is about 2 to 6 films of quarter wavelength thicknesses of alternating materials having different indices of refraction. IF layer 54 is a stack of half wavelength films of alternating materials having different indices of refraction. Wafer 52 is brought into proximity with wafer 46 upon contact of spacers 50 on wafer 46 at a peripheral surface of wafer 52 to form a thermally isolating space 55. The first or second side of wafer 52 may be closest to wafer 46; however, FIG. 2 shows the first side of wafer 52 closest to wafer 46. A 500 micron silicon detector wafer 56 is formed on wafer 52. Wafer 56 is etched to create a cavity 57 in the middle with portions of wafer 56 being proximate to wafer 52 at the periphery of wafer 52. At one side on the periphery of wafer 56 is formed a flow sensor 58 which is electrically connected externally with contacts 59 on wafer 56 to leads 60. Wafer 56 has a via 61 etched near flow sensor 58 to facilitate the flow of gas or air 62 by flow sensor 58. A solder ring 63 is formed on the outer periphery of wafer 56. A top cap wafer 64 is formed on solder ring 63 proximate to wafer 56. The central portion of wafer 64 is etched to form cavity 57 in conjunction with wafer 56. There is about an 18 micron via or flow channel 65 that is formed between wafers 56 and 64 so that air or gas 62 can flow back and forth between cavity 57, past flow sensor 58, and through via 61 to an environment external of gas sensor 45. Formed on wafer 64 is a porous filter layer 66 which forms a wall of cavity 57. Filter 66 allows ambient gas 67 of the environment external to gas sensor 45 to infiltrate or diffuse in and out of cavity 57 to equalize the concentration of the ingredients of the gases and air. Layer 66 may be a wafer with pores etched in it but here it is a stainless steel frit which is porous. The stainless steel frit is compressed to attain the correct porosity for gas sensor 45. The frit may have 2 micron pores covering about 40–50 percent of the frit area, and be about 50 microns thick.

The function of sensor 45 is to detect the magnitude of $CO_2$ in the ambient atmosphere. Light source 47 has an electrical AC signal at a frequency up to about 100 hertz applied to it. Light source 47 emanates radiation 51 that is composed mainly of IR light. Radiation 51 has a varying or pulsing magnitude or intensity at the frequency of the electrical AC signal applied to source 47. Fluctuating or pulsing light 51 passes through space 55 and AR layer 53 and into wafer 52. From wafer 52, light 51 passes through narrow band pass filter 54 which filters out effectively all of the wavelengths of light 51 except that of 4.3 microns which is the absorption wavelength of $CO_2$. The 4.3 micron light 51 enters cavity 57. If $CO_2$ gas 67 infiltrates through filter 66 into cavity 57, $CO_2$ gas 67 heats up during the period it absorbs the light and cools down when light 51 is not present during the minimum magnitude of the period of the fluctuating or pulsing of light 51. During absorption of light 51 by gas 67, gas 67 heats up and expands in volume thereby forcing a flow 62 out of cavity 57 through channel 65, by flow sensor 58 and out of sensor 45 through via 61. If cavity 57 is a resonator optically or acoustically tuned to the absorption wavelength, the effects of the light or sound upon the absorbing gas is greatly increased resulting in much improved detection of very small amounts of gas 67. Acoustic resonator techniques may also be used. In the periodic absence of light 51, gas 67 stops absorbing light and cools down. Then gas 67 contracts in volume thereby causing a flow 62 into sensor 45 through via 61, by flow sensor 58 and through channel 65 into cavity 57. Thus, there is a fluctuation of gas 67 and respective flow 62 over flow sensor 58 that corresponds to the fluctuation of light 51. The porosity of filter 66 is small enough so as not to prevent pressure pulsations or flow 62 from happening through or by flow sensor 58. Flow sensor 58 outputs a signal that is indicative of and proportional to the amount, magnitude, or velocity of flow 62 going through or by sensor 58. Sensor 58 measures a flow 62 rate in cubic centimeters per second. The amount, magnitude, or velocity of flow 62 is proportional to the amount of $CO_2$ gas 67 present in cavity 57 and immediately external to gas sensor 45. The presence of any other gas in absence of $CO_2$ does not cause any pressure pulsations or flow 62 or any fluctuation of flow 62 because there is no absorption of the 4.3 micron light 51 when it enters cavity 57. Thus, the signal from flow sensor 58 is indicative of the amount of $CO_2$ gas 67 present around gas sensor 45. A processor 68, which is connected to flow sensor 58, inferentially determines from the amount of $CO_2$ gas 67, the presence and amounts of the various toxic gases that are in the ambient environment immediately around and about micromachined inferential toxic gas indicator 45. The signal from flow sensor 58, indicating an amount of concentration of gas or liquid having an absorption wavelength goes to processor 68. Processor 68 has a table of information that indicates certain amounts of concentrations of particular gases or liquids, which infer the presence of certain amounts of concentrations of combustion products. The presence of certain amounts of concentrations of combustion products are more accurately inferred by the presence of certain amounts of concentrations of the particular gases or liquids because the latter amounts of concentrations are up to several magnitudes larger than the certain amounts of concentrations of combustion products. Processor 68 processes the signal from flow sensor 58 and may provide inferred information indicative of a presence of other gases or liquids and/or future or present or past chemical or physical activity.

Figure 3:
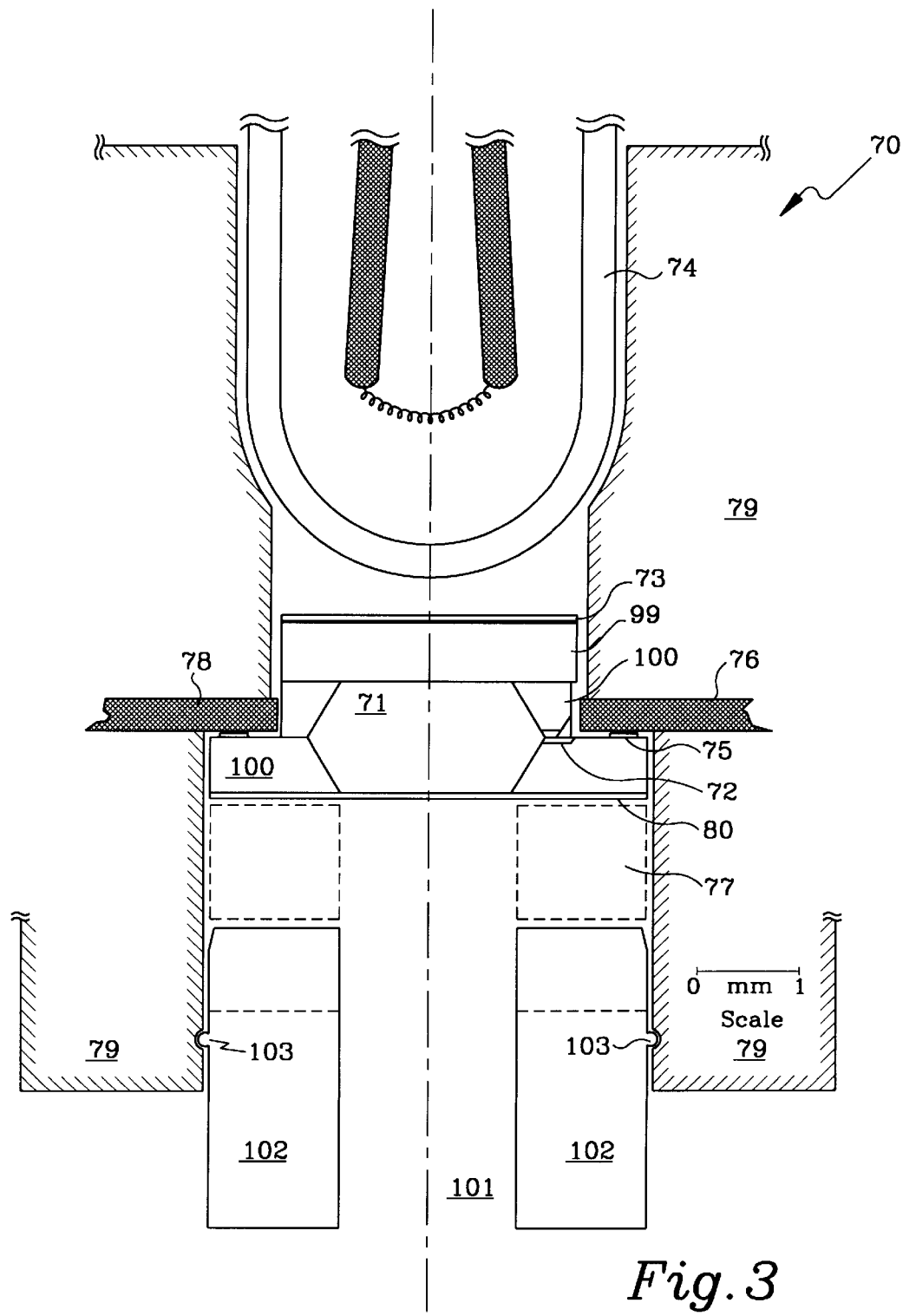
FIG. 3 shows a microsensor hybrid design in which the flow sensor and the narrow band pass filter reside on one micromachined block.

If light source 47 were to be an incandescent minitungsten filament lamp, like source 74 in FIG. 3, the effective rate of the AC excitation signal would be about 10 hertz. An increased frequency would result in less effectiveness on the expansion and absorption of the gas. A DC signal result in no detection of the light absorbing gas 67. The present integrated circuit light source 47 can effectively be cycled or pulsed up to 100 hertz which results in greater sensitivity of sensor 45. The sensitivity increase is equal to the square root of the ratio of the effective frequencies of the two light sources which is about 3.16, that is, the square root of 100/10.

Gas sensor 45 may be designed to directly detect and indicate the presence of other gases or liquids besides $CO_2$. Narrow band pass filter 54 could be changed to a filter that would pass a different wavelength of light 51 which would be equivalent to the absorption wavelength of another kind of gas to be detected and measured. For instance, filter would be designed to pass 4.6 micron wavelength of light if CO were to be detected by sensor 45 or to a wavelength from 3.2 to 3.4 microns if a gas or liquid having hydrocarbon (CH) bonds were to be detected by sensor 45. Another change or adjustment that would better facilitate detection of a specific gas or liquid would be that of diffusion filter 66. For example, adjustment of the porosity of stainless steel frit or filter 66 may achieve by the amount of compression that is applied to frit 66. Compressing frit 66 causes it to be less porous and increases the signal-to-noise ratio of the output of flow sensor 58. This ratio increases because the reduced porosity or freedom of flow through filter 66 results in a crisper flow 62 over flow sensor 58 when gas 67 is expanding and contracting in response to the absorption of fluctuating light 51. However, the response time to the measurement of the immediate presence of gas 67, external to sensor 45, is slower since the infiltration of gas 67 into cavity 57 is much slower because of the more restrictive or less porous filter 66 to ambient gas.

FIG. 3 shows an overview of a low-cost opto-flow sensor 70, which is a $CO_2$ microsensor hybrid design, in which a sensor cell 71, flow detector 72 and IR filter 73 on glass 99 reside on one micromachined silicon block 100 in a plastic housing 79. Glass plate 99 could be replaced with a silicon wafer. Light bulb 74 is integrated into this design. Chip contact pads 75 are pressed towards lead frame wires 76 by felt-metal spring-washer 77. This package features direct contact between the chip and lead frame 76 embedded in plastic molding 79, thus saving the cost of wire bonding or the unreliability/noise of the zebra strip contacts, depending on the reference, the integration of flow sensor 72 into sensor cavity 71, chip 78 held in place, not with an unstable material such as an elastomer, but with a more stable one such as stainless steel 80, selected light source 74 is operated at an AC voltage level that causes the peak output to be no less than the peak level after suitable (90%) derating; this is to achieve a combination of maximum life and maximum output at the highest practical frequency near 100 Hz. Sensor 70 is plugged to a tube 100 with housing 102, which also functions as a stop against felt-metal spring-washer 77, from which the gas or air to be monitored comes. Plastic or steel snaps 103 secure sensor 70 to tube 101.

Figure 4:
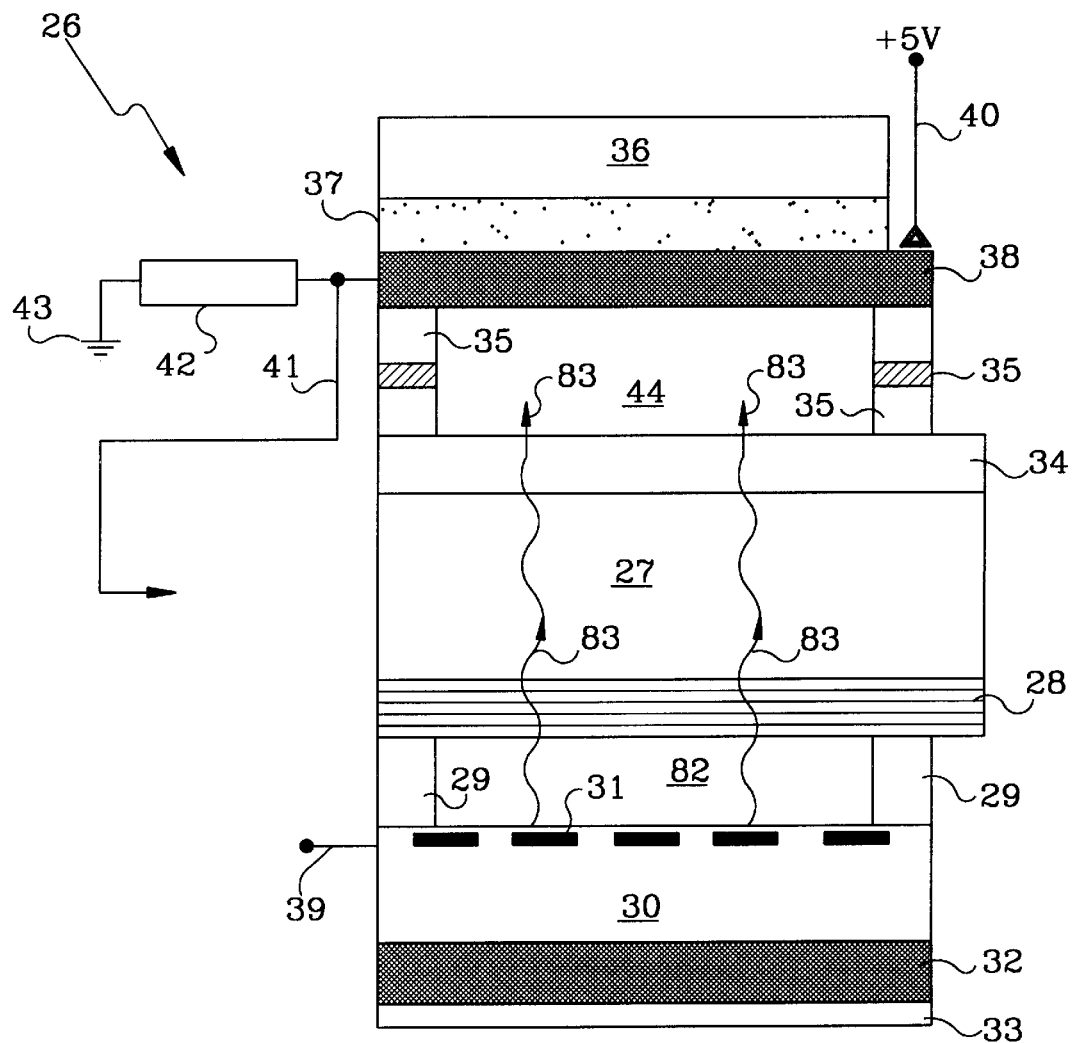
FIG. 4 reveals an integrated opto-acoustic gas sensor.

FIG. 4 is another structure of gas sensor 26. Silicon substrate 27 is formed to be as thin as possible to maximize optimal efficiency. A multilayer narrow band pass IF 28 for a 4.3 micron wavelength is formed on a first side of Si substrate 27. Spacers 29 are formed on the periphery of IF layer 28. Layer 28 may be a wafer of silicon or other appropriate material, or a glass plate. A one micron silicon nitride support 30 is formed. A 0.1 micron heater serpentine or IR light source 31 is formed or embedded in layer 30. Spacers 29 are formed on the periphery of the heater side of support layer 30. Supports 29 of layers 28 and 30 are brought together to form a 2 micron evacuated or air-filled cavity 82 for thermal isolation between layers 30 and 28. A 0.1 to 0.3 micron Au reflective coating layer 32 is formed on the other side of layer 30, not supporting heater or IR light source 31. A 0.1 micron silicon layer 33 is formed on layer 32 to protect the Au film. An AR coating layer 34 for a 4.3 micron wavelength is formed on the second side of substrate 27, opposite of the first side having IF layer 28 formed on it. A porous support 35 is formed on the periphery of layer 34. A 1 to 2 micron polysilicon layer 36 is formed. A 0.1 to 0.3 micron piezoresistive sensor film layer 37 is formed on layer 36, and a 0.1 to 0.2 micron Au reflective coating layer 38 is formed on layer 37. Porous support 35 is formed also on the periphery of layer 38. Support 35 with layers 34 and 38 form a gas cavity 44 having about 2 microns between layers 34 and 38. An electrical alternating current (AC) input terminal 39 is connected to heater or light source 31. A plus 5 volt terminal 40 is connected to a first end of layer 38, and an output terminal 41 is connected to a second end of layer 38. A load resistor or reactance 42 is connected between output terminal 41 and a reference voltage 43.

Air and/or gas from the ambient environment about sensor 26 diffuse into cavity 44 via porous spacer 35. Spacer 35 may be silicon or other material with tiny etched holes; alternately, spacer 35 may also be a porous stainless steel frit. Functionally, light source 31 is activated and emanates light with a charging or pulsing intensity between 10 to 100 hertz. If source 31 were an incandescent light the rate would be closer to 10 hertz but if it were an array of microheaters as in FIG. 2, the rate could approach 100 hertz. Light 83 goes through narrow band pass filter 28, silicon substrate 27 and antireflective (AR) coating 34, into cavity 44 containing the gas, if any, to be detected, which diffuses into cavity 44 through porous spacer 35. Instead of spacer 35 being porous, layers 36, 37, and 38 could be replaced with a porous layer such as that of silicon or a stainless steel frit. The piezoresistive sensor film could be on a portion of the porous layer or frit, or in the vicinity of spacer 35. The narrow band pass filter and the AR coating are designed for the absorption wavelength of the gas to be detected. When light 83 in cavity 44 has the same wavelength as the absorption wavelength of a gas present in cavity 44, the gas heats up upon absorption of light 83. The gas expands and increases the pressure within cavity 44. The pressure causes piezoresistive layer or sensor 37 to bend or distort and output a voltage indication at output 41. When light 83 decreases in intensity or is off, the gas cools resulting in a cavity 44 pressure decrease thereby causing piezoresistive element 37 to bend or distort in the opposite direction or way. The magnitude of the voltage from sensor 37 is an indication of the amount of concentration of gas in cavity 44, and about the environment ambient to sensor 26. The porosity of spacer 35 or the layer in lieu of layers 36–38, needs to be sufficiently minimal so that a detectable pressure can be created in cavity 44 when light impinges and is absorbed by the detected gas. This gas detector 26 is regarded as an opto-acoustic sensor having a microphone-like detection.

FIG. 5 shows another version of an opto-acoustic sensor. A 3.0 micron interference narrow band pass filter 88 for a wavelength of 4.3 microns is formed on a first surface of a 250 micron silicon substrate 89. Layer 89 may be instead a glass plate. A 2.0 micron anti-reflective coating 90 is formed on a second surface, i.e., the other side of silicon substrate 89. An antireflective (AR) coating may also be formed on filter 88. Heater 86 may be formed in a one micron, polysilicon layer 87 which is formed on filter 88 of substrate 89. A 0.1 micron reflective coating 98 for a 4.3 micron wavelength light is formed on the surface of layer 87.

Polysilicon layer 87 is formed resulting in a 2 micron cavity 91, with a sacrificial layer on layer 88. The sacrificial layer is removed. Cavity 91 provides thermal insulation between heater 86 and substrate 89. A 2.0 micron sacrificial layer is formed and etched on the AR side of substrate 89 for a 2.0 micron cavity 92 as done for cavity 91. A 0.1 micron reflective coating 94 for a wavelength of 4.3 microns is formed on the sacrificial layer. A 0.1 micron piezoresistive film 93 is formed partially on coating 90, coating 94 and the sacrificial layer for cavity 92. A 2.0 micron polysilicon layer 95 is formed partially on piezoelectric layer 93, reflective coating 94 and the sacrificial layer for cavity 92.

Small (0.1 micron) holes 96 are etched in polysilicon layer 95 so that the sacrificial layer can be removed to result in cavity 92. Holes 96 also form the porous wall of cavity 92 so that air and/or gas of the ambient environment of sensor 85 may diffuse into cavity 92. Heater 86 emits light 97 that goes through layers 87, 88, 89 and 90 into cavity 92. If there is a gas having an absorption wavelength of 4.3 microns, it heats up and the increased pressure bends piezoresistive element 93 which produces an electrical signal. Heater 86 emits light 97 having a varying or pulsing intensity which causes the gas to heat up and cool. This cycling is sensed by element 93. The magnitude of such cycling is an indication of the amount of concentration of the gas, e.g., $CO_2$, in cavity 92 and in the ambient environment of sensor 85.

What is claimed is:

1. A micromachined integrated gas/liquid sensor comprising:
    a wafer;
    a light source formed on said wafer;
    a layer formed on said wafer;
    an optical filter formed on said layer;
    a cavity formed on said layer;
    a flow sensor formed proximate to said cavity; and
    a porous filter formed on said cavity.
2. The sensor of claim 1 wherein said layer is glass.
3. The sensor of claim 2 wherein:
    said optical filter is a narrow band pass filter for passing light from said light source, passes a first wavelength into said cavity; and
    a gas or liquid to be sensed has an absorption wavelength at the first wavelength.
4. The sensor of claim 3 wherein:
    the gas or liquid in an ambient environment about the sensor will infiltrate through said porous filter into said cavity;
    light that may come from said light source and pass through said optical filter into said cavity has an intensity that increases and decreases;
    the gas or liquid in said cavity and impinged by the light from said optical filter, will expand and contract if the gas or liquid has an absorption wavelength at the first wavelength;
    the gas or liquid in said cavity and impinged by the light from said optical filter, will not expand and contract if the gas or liquid has an absorption wavelength not at the first wavelength; and
    said flow sensor can sense an expansion or contraction of the gas or liquid.
5. The sensor of claim 4 wherein said porous filter is a compressed metal frit.
6. The sensor of claim 5 wherein:
    said flow sensor can output a signal that indicates a magnitude of the expansion or contraction of the gas or liquid; and
    the magnitude of the expansion or contraction indicates an amount of concentration of the gas or liquid having an absorption wavelength at the first wavelength, in said cavity and in turn in the ambient environment of the sensor.
7. The sensor of claim 6 further comprising a processor, wherein:
    the signal from said flow sensor, indicating an amount of concentration of the gas or liquid having an absorption wavelength at the first wavelength, goes to said processor; and
    said processor processes the signal from said flow sensor and provides inferred information.
8. The sensor of claim 7 wherein the first wavelength is at an absorption wavelength of CO.
9. The sensor of claim 7 wherein the first wavelength is at an absorption wavelength of $CO_2$.
10. The sensor of claim 9 wherein
    said processor comprises a table of information.
11. The sensor of claim 7 further comprising an integrated circuit formed on said wafer and wherein said integrated circuit has a processor.
12. The sensor of claim 11 further comprising an antireflective coating for the first wavelength formed on said layer.
13. The sensor of claim 1 wherein said layer is a wafer.
14. A micromachined integrated circuit gas/liquid sensor comprising:
    a first layer;
    a set of microemitters formed on a first surface of said first layer;
    a second layer;
    a narrow band pass filter for a first wavelength formed on a first surface of said second layer;
    a third layer;
    a fourth layer having a first surface adjacent to a first surface of said third layer, wherein said third and fourth layers have central portions removed to form a cavity;
    a channel formed in at least one first surface of said third and fourth layers, from the cavity to an outer edge of said third and fourth layers;
    a detector formed in said channel;
    a porous filter layer formed on a second surface of said fourth layer; and
    wherein:
        the first surface of said first layer is adjacent to a second surface of said second layer; and
        the first surface of said second layer is adjacent to a second surface of said third layer.
15. The sensor of claim 14 wherein said porous filter layer is a frit having appropriately low porosity.
16. The sensor of claim 15 wherein:
    said first, third, and fourth layers are wafers; and said second layer is a glass plate.

17. The sensor of claim 16 further comprising:

a first through-the-layer contact formed on a second surface of said first layer and through said first layer to said set microemitters; and a second through-the-layer contact formed on the second surface of said first layer and through said first, second, and third layers to said detector.

18. The sensor of claim 17 further comprising an integrated circuit formed on the second surface of said first layer.

19. The sensor of claim 18 further comprising an antireflective coating formed on the second surface of said second layer.

20. The sensor of claim 19 wherein:

the gas or liquid in an ambient environment about the sensor will infiltrate through said porous filter layer into the cavity;

light that may come from said set of microemitters and pass through said narrow band pass filter into the cavity has an intensity that is modulated;

the gas or liquid in the cavity and impinged by the light passing through said narrow band pass filter, will change in temperature, pressure, and volume, in that order, if the gas or liquid has an absorption wavelength at the first wavelength;

the gas or liquid in the cavity and impinged by the light passing through said narrow band pass filter, will not have a change of volume caused by the light if the gas or liquid has an absorption wavelength not at the first wavelength; and said detector can sense a change of volume of the gas or liquid.

21. The sensor of claim 20 wherein:

said detector can output a signal that indicates a magnitude of the change of volume of the gas or liquid; and the magnitude of the change of volume indicates an amount of concentration of the gas or liquid having an absorption wavelength at the first wavelength, in the cavity and in turn in the ambient environment of the sensor.

22. The sensor of claim 21 further comprising a processor, wherein:

the signal from said detector, indicating an amount of concentration of the gas or liquid having an absorption wavelength at the first wavelength, goes to said processor; and said processor processes the signal from said detector and provides inferred information.

23. The sensor of claim 22 wherein said processor comprises a table of information.

24. The sensor of claim 23 wherein:

the first wavelength is at an absorption wavelength of $CO_2$; and the presence of $CO_2$ indicates the presence of certain combustion products.

25. The sensor of claim 15 wherein said first, second, third, and fourth layers are wafers.

26. The sensor of claim 15 wherein said frit has a porosity that may be decreased with increased compression of said frit or increased with decreased compression of said frit, for optimal porosity.

27. Means for sensing a gas or liquid, comprising:

means for providing radiation;

means for filtering radiation, proximate to said means for providing radiation;

means for containing the gas or liquid, proximate to said means for filtering radiation;

first means for permitting the gas or liquid to enter or leave said means for containing the gas or liquid, proximate to said means for containing the gas or liquid;

second means for permitting the gas or liquid to enter or leave said means for containing the gas or liquid, proximate to said means for containing the gas or liquid; and means for detecting a rate of flow of the gas or liquid in or out of said means for containing the gas or liquid, proximate to said second means for permitting the gas or liquid to enter or leave means for containing the gas or liquid; and wherein:

said means for filtering radiation is a narrow band pass filter for passing radiation at a first wavelength;

radiation from said means for providing radiation has a varying intensity;

the gas or liquid having an absorption of radiation at the first wavelength will vary in temperature, pressure, and volume, in that order, due to absorption of radiation having a varying intensity; and said means for detecting a rate of flow of the gas or liquid in or out of said means for containing the gas or liquid, will detect a variation in volume of the gas or liquid in said means for containing the gas or liquid.

* * * * *